(12) United States Patent
Begley et al.

(10) Patent No.: US 7,049,012 B2
(45) Date of Patent: *May 23, 2006

(54) ORGANIC ELEMENT FOR ELECTROLUMINESCENT DEVICES

(75) Inventors: William J. Begley, Rochester, NY (US); Tukaram K. Hatwar, Penfield, NY (US); Manju Rajeswaran, Fairport, NY (US); David J. Giesen, Webster, NY (US); Natasha Andrievsky, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/701,241

(22) Filed: Nov. 4, 2003

(65) Prior Publication Data

US 2005/0095453 A1 May 5, 2005

(51) Int. Cl.
*H05B 33/14* (2006.01)

(52) U.S. Cl. ............ 428/690; 428/917; 313/504; 313/506; 257/98

(58) Field of Classification Search .......... 428/690, 428/917; 313/504, 506
See application file for complete search history.

(56) References Cited

U.S. PATENT DOCUMENTS

| 6,387,547 B1 | 5/2002 | Fujita et al. | |
| 6,399,223 B1 | 6/2002 | Fujita et al. | |
| 2003/0099860 A1* | 5/2003 | Lin et al. | 428/690 |

FOREIGN PATENT DOCUMENTS

| EP | 1 148 109 | 10/2001 |
| JP | 04-335087 | 11/1992 |
| JP | 10289786 | 10/1998 |
| JP | 2000-156290 | 6/2000 |

OTHER PUBLICATIONS

Co-pending, commonly assigned, concurrently filed, U.S. Appl. No. 10/701,040 titled "Organic Element For Electroluminescent Devices", of Begley et al.
Co-pending, commonly assigned, concurrently filed, U.S. Appl. No. 10/700,894, titled "Organic Element For Electroluminescent Devices", of Begley et al.
Co-pending, commonly assigned, concurrently filed, U.S. Appl. No. 10/700,916, titled "Organic Element For Electroluminescent Devices", of Begley et al.

* cited by examiner

Primary Examiner—Dawn L. Garrett
(74) Attorney, Agent, or Firm—Arthur E. Kluegel

(57) ABSTRACT

Disclosed is an OLED device comprising a light-emitting layer (LEL) containing a host and a dopant located between a cathode and an anode wherein the emitter is an orange-red light emitting rubrene derivative represented by formula (I):

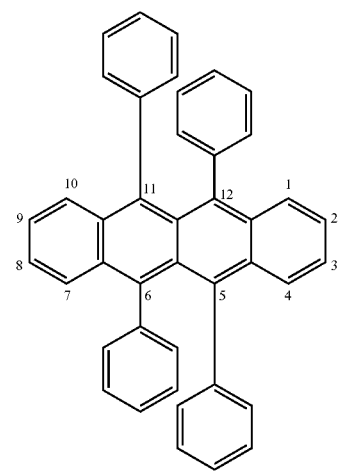

Formula (I)

wherein:
a) there are identical oxy, aza or thio groups at the 2- and 8-positions;
b) the phenyl rings in the 5- and 11-positions contain only para-substituents identical to the oxy, aza or thio groups in paragraph a);
c) the phenyl rings in the 6- and 12-positions are substituted; and
provided that when a single substituent on both phenyl rings in paragraph c) are present, said substituent is not a methoxy group located at the para-position.

36 Claims, 1 Drawing Sheet

ORGANIC ELEMENT FOR ELECTROLUMINESCENT DEVICES

FIELD OF INVENTION

This invention relates to organic light emitting diode (OLED) electroluminescent (EL) device comprising a light-emitting layer containing a rubrene dopant compound containing an oxy, aza or thio group attached to the end rings of the naphthacene nucleus.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322–334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the organic EL element encompasses the layers between the anode and cathode electrodes. Reducing the thickness lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. The interface between the two layers provides an efficient site for the recombination of the injected hole/electron pair and the resultant electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610–3616, 1989]. The light-emitting layer commonly consists of a host material doped with a guest material—dopant, which results in an efficiency improvement and allows color tuning.

Since these early inventions, further improvements in device materials have resulted in improved performance in attributes such as color, stability, luminance efficiency and manufacturability, e.g., as disclosed in U.S. Pat. Nos. 5,061,569, 5,409,783, 5,554,450, 5,593,788, 5,683,823, 5,908,581, 5,928,802, 6,020,078, and 6,208,077, amongst others.

Notwithstanding these developments, there are continuing needs for organic EL device components, such as dopants, that will provide high luminance efficiencies combined with high color purity and long lifetimes.

A useful class of dopants is that derived from 5,6,11,12-tetraphenylnaphthacene, also referred to as rubrene. The solution spectra of these materials are typically characterized by wavelength of maximum emission, also referred to as emission $\lambda_{max}$, in a range of 550–560 nm and are useful in organic EL devices in combination with dopants in other layers to produce white light. However, the range of light emitted by rubrene derived dopants limits the purity of the white light produced in OLEDs. In order to achieve OLEDs that can produce higher purity white light, one needs to have the ability to increase the range of maximum emission, or emission $\lambda_{max}$ of the rubrene derived dopants so that they can be matched spectrally with the emission of dopants in the other light producing layers. Useful dopants are those that emit light in solution in the range of 560–650 nm, and particularly in the 565–600 nm range, have good efficiency and sublime readily.

Yellow light is generally defined as having a wavelength range in the visible region of the electromagnetic spectrum of 570–590 nm, orange light 590–630 nm and red light 630–700 nm, as defined by Dr. R. W. G. Hunt in *The Reproduction of Colour in Photography, Printing & Television*, 4$^{th}$ Edition 1987, Fountain Press, page 4. When light has a spectral profile that overlaps these ranges, to whatever degree, it is loosely referred to as yellow-orange or orange-red.

U.S. Pat. Nos. 6,387,547; 6,399,223; EP 1,148,109A2, and JP20001156290A teach the use of rubrene derivatives containing either 2 phenyl groups on one end ring of the rubrene structure or 4 phenyl groups on both end rings. There is no teaching of oxy, aza or thio groups on each end ring of the rubrene structure.

JP 04335087 discloses specific compounds 3 and 4. Compound 3 contains two methoxy groups diagonally opposite each other on two of the central phenyl rings of the rubrene molecule. Compound 4 contains six methoxy groups; four on the central phenyl rings and two on either end rings of the rubrene. Compounds 3 and 4 fall outside the scope of the invention. These rubrene derivatives do not produce the desired emission $\lambda_{max}$. Thus devices containing these rubrene derivatives fail to provide white OLED devices with high color purity.

The problem to be solved is to provide a dopant compound for a light-emitting layer of an OLED device that provides white light purity, high luminance efficiency and sublimes readily.

SUMMARY OF THE INVENTION

An OLED device comprising a light-emitting layer (LEL) containing a host and a dopant located between a cathode and an anode wherein the emitter is an orange-red light emitting rubrene derivative represented by formula (I):

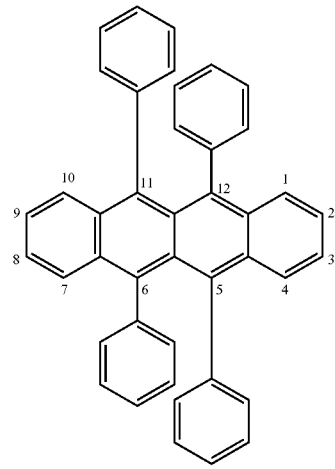

Formula (I)

wherein:
a) there are identical oxy, aza or thio groups at the 2- and 8-positions;
b) the phenyl rings in the 5- and 11-positions contain only para-substituents identical to the oxy, aza or thio groups in paragraph a);
c) the phenyl rings in the 6- and 12-positions are substituted; and
provided that when a single substituent on both phenyl rings in paragraph c) are present, said substituent is not a methoxy group located at the para-position.

The invention also provides a display including such a device and a method of imaging using such a device.

Such a device exhibits long wavelength electroluminescence desirable in the production of high purity white light.

DETAILED DESCRIPTION OF THE INVENTION

Figure 1:
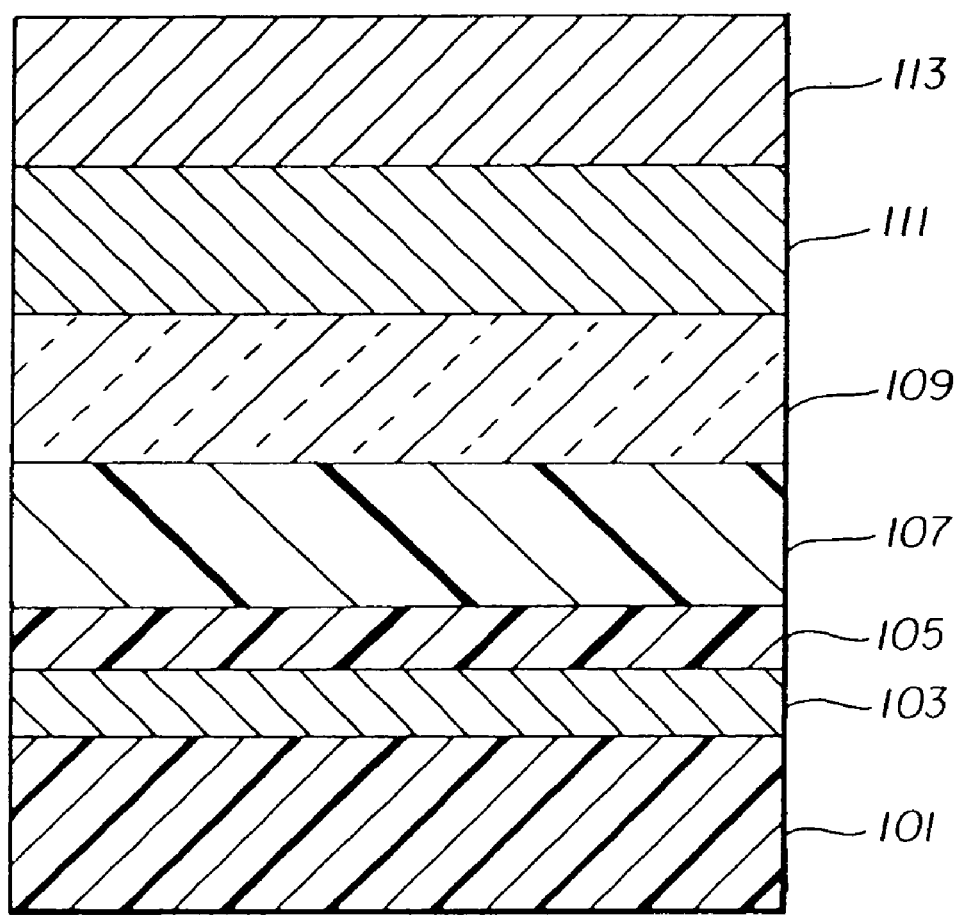
FIG. 1 shows a cross-section of a typical OLED device in which this invention may be used.

The invention is generally as described above.

An OLED device of the invention is a multilayer electroluminescent device comprising a cathode, an anode, charge-injecting layers (if necessary), charge-transporting layers, and a light-emitting layer (LEL) comprising a host and at least one dopant, a rubrene compound. The term rubrene refers to 5,6,11,12-tetraphenylnaphthacene as defined by the *Grant & Hackh's Chemical Dictionary*, Fifth Edition, McGraw-Hill Book Company, page 512 and *Dictionary of Organic Compounds*, Fifth Edition, Chapman and Hall, Volume 5, page 5297. The term naphthacene is the chemical name used to describe four linearly fused benzene rings as defined by the *Grant & Hackh's Chemical Dictionary*, Fifth Edition, McGraw-Hill Book Company, page 383.

Suitably, the light-emitting layer of the device comprises a host and dopant where the dopant is present in an amount of up to 10%-wt of the host, more typically from 0.1–5.0%-wt of the host. The dopant is suitably a 5,6,11,12-tetraphenylnaphthacene with oxy, aza or thio groups in the 2,8-positions of the naphthacene, and usefully a 5,6,11,12-tetraphenylnaphthacene with oxy groups in the 2,8-positions of the naphthacene. Good results are obtained when the phenyl, oxy, aza or thio groups are substituted, particularly where the substituent groups are fluorine, fluorine containing groups, alkyl, aryl, alkoxy or aryloxy groups.

Useful dopants of the invention are those that emit light in ethyl acetate solution such that 560 nm<$\lambda_{max}$≦650 nm and preferable 565 nm<$\lambda_{max}$≦625 nm and in the EL device such that 570 nm<$\lambda_{max}$≦650 nm with good efficiency. Combined with other light emitting dopants, the dopants of the invention can be used to produce white light. The other light emitting dopants are usefully dopants that emit blue or blue-green light.

Blue light is generally defined as having a wavelength range in the visible region of the electromagnetic spectrum of 450–480 nm, blue-green 480–510 nm, green 510–550, green-yellow 550–570 nm, yellow 570–590 nm, orange 590–630 nm and red 630–700 nm, as defined by Dr. R. W. G. Hunt in *The Reproduction of Colour in Photography, Printing & Television*, 4$^{th}$ Edition 1987, Fountain Press, page 4. Suitable spectral combinations of these components produce white light.

Another embodiment of the invention comprises additional layers incorporating dopants the light from which, in combination with the orange-red light of the rubrene derivative combine to give white light. Such additional dopants can be chosen so that they emit blue or blue-green light.

In another embodiment of the invention when additional layers are present so that the emitted light is white, a filter capable of controlling the spectral components of the white light such as red, green and blue, can be placed over-lying the device to give a device useful for color display. Suitably, each light-emitting layer of the device comprises a host and dopant where the dopant is present in an amount of up to 10%-wt of the host, more typically from 0.1–5.0%-wt of the host The benefit imparted by the dopant does not appear to be host specific. Desirable hosts include those based on amine compounds. One particularly example of a host is N,N'-di-1-naphthalenyl-N,N'-diphenyl-4,4'-diaminobiphenyl (NPB)

Embodiments of the dopants useful in the invention provide an emitted light having an orange-red hue. In combination with the dopants of the invention, additional dopants that emit blue or blue-green light in additional layers, results in- the formation of white light. Substituents on the dopants of the invention are selected to provide embodiments that exhibit a reduced loss of initial luminance compared to the device containing no rubrene compound.

Formula (II) suitably represents compounds useful in the invention:

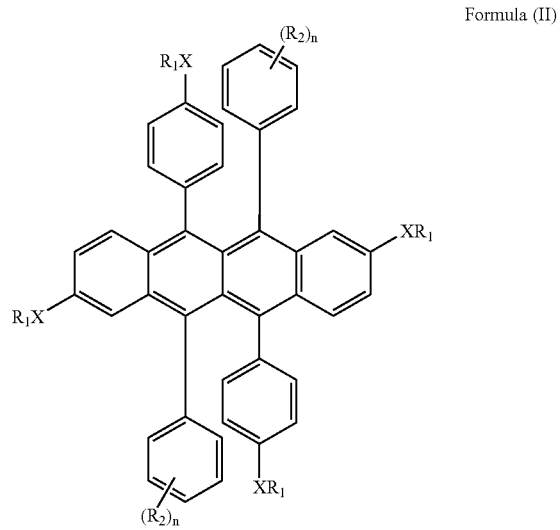

Formula (II)

wherein
$R_1$ is selected from alkyl, carbocyclic, and heterocyclic groups;
$R_2$ is a substituent group;
X is oxygen, sulfur or N($R_3$) wherein $R_3$ is selected from alkyl, carbocyclic and heterocyclic groups or taken with $R_1$ may form a ring;
n is 0–5;
provided that all $R_1$ groups are the same;
provided further, that the $R_2$, their location and n value on one ring are the same as those on the second ring; and
provided still further that when X is oxygen and n is 1, $R_2$ is not para-methoxy.

When X is oxygen, particularly useful compounds of the invention are represented by formula (III):

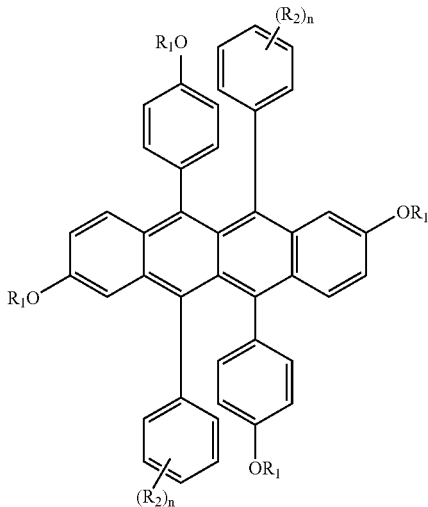

Formula (III)

Further useful embodiments of the invention are represented by formula (IV):

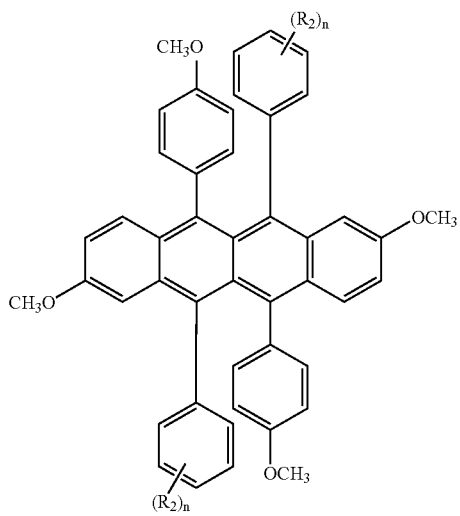

Formula (IV)

wherein
R$_2$ is a substituent group;
n is 0–5;
provided that the R$_2$, their location and n value on one ring are the same as those on the second ring; and
provided further that when n is 1, R$_2$ is not para-methoxy In formulae (II) and (IV) useful in the device, all R$_1$ groups are the same and are conveniently alkyl, carbocyclic and heterocyclic groups. Particularly useful R$_1$ groups are alkyl groups. The alkyl groups can be represented by formula:

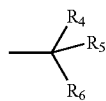

wherein each of R$_4$, R$_5$ and R$_6$ is hydrogen or an independently selected substituent. R$_4$, R$_5$ and R$_6$ taken together may form a mono- or multi-cyclic ring system. Particularly useful R$_4$, R$_5$ and R$_6$ groups can be selected from hydrogen, alkyl and carbcyclic groups with no more than one being hydrogen. The R$_4$, R$_5$ and R$_6$ groups may be further substituted with halide, particularly fluorine or fluorine containing groups such as trifluoromethyl, alkyl, aryl, alkoxy, and aryloxy groups. The X groups can be selected from oxygen also referred to as oxy, sulfur also referred to as thio, and N(R$_3$) also referred to as aza groups, but preferably from oxygen and sulfur. The R$_1$ and R$_3$ groups can be independently selected from alkyl, carbocyclic and heterocyclic groups, or taken together R$_1$ and R$_3$ may form a 5- or 6-membered ring. In the device, the R$_2$ groups on one phenyl group are the same as those on the diagonally opposite phenyl group, in terms of location and number. The term "diagonally opposite phenyl group" refers to the location of the phenyl groups on the naphthacene nucleus. The phenyl groups in the 5- and 11-positions or the 6- and 12-positions are diagonally opposite each other. The R$_2$ groups are selected from the group consisting of halide, alkyl, aryl, alkoxy, and aryloxy groups. In one useful embodiment, the R$_2$ groups are selected from the group consisting of fluorine, alkyl, and aryl groups. A desirable embodiment is where R$_2$ is fluorine or a fluorine-containing group such as trifluoromethyl, pentafluoroethyl and fluorinated-phenyl. The R$_2$ groups may be located in the ortho, meta and para positions on the phenyl ring, but preferably in the meta and para positions. When R$_2$ is fluorine it can be located in either of the ortho, meta or para positions, or it may be located in any combination of these positions or in all of these positions.

The emission wavelength of these compounds may be adjusted to some extent by appropriate changes to R$_1$, R$_2$, R$_3$, R$_4$, R$_5$ and R$_6$ groups to meet a color aim, namely orange-red.

The rubrene compound is usually doped into a host compound, which represents the light-emitting layer between the hole-transporting and electron-transporting layers. The host is chosen such that there is efficient energy transfer from the host to the rubrene compound. The rubrene compound emits from the excited state to afford a bright, highly-efficient, stable EL device.

The EL device of the invention is useful in any device where light emission is desired such as a lamp or a component in a static or motion imaging device, such as a television, cell phone, DVD player, or computer monitor.

Illustrative examples of rubrene compounds useful in the present invention are the following:

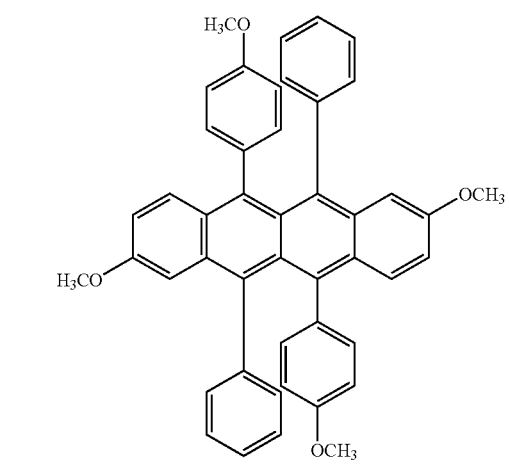

Inv-1

-continued
Inv-2
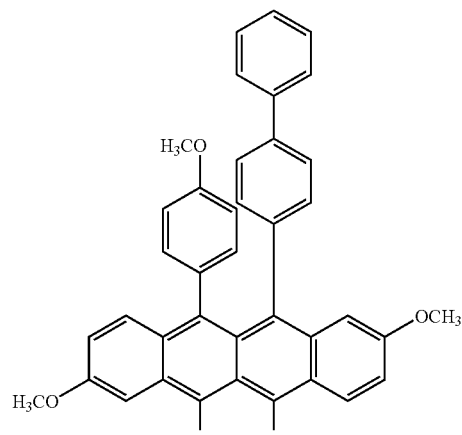
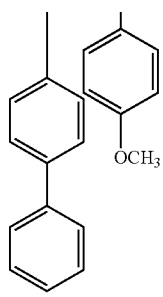
Inv-3
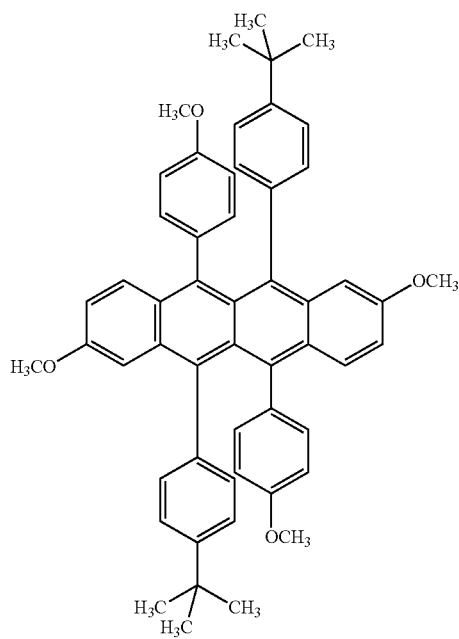
Inv-4
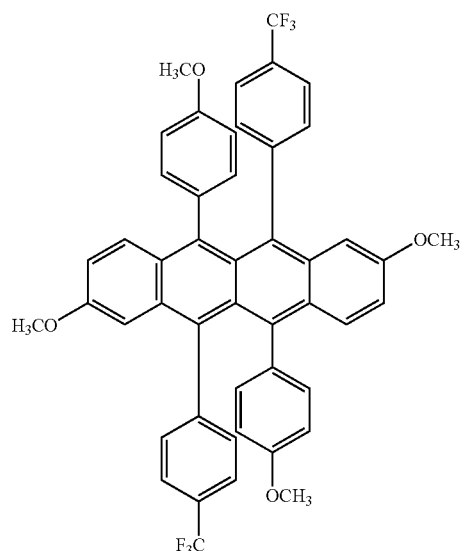
Inv-5
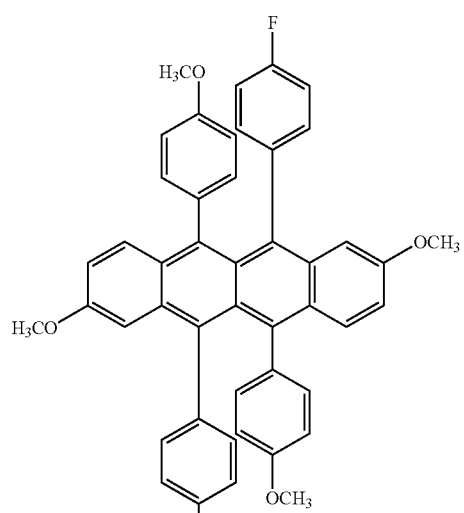
Inv-6
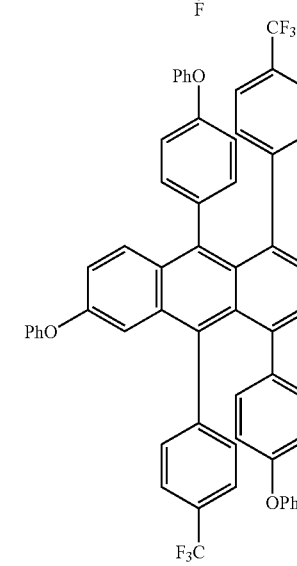
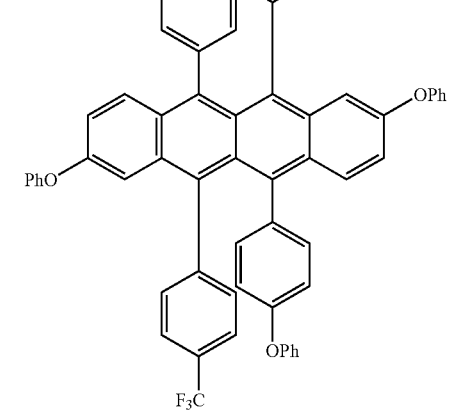

-continued
Inv-7
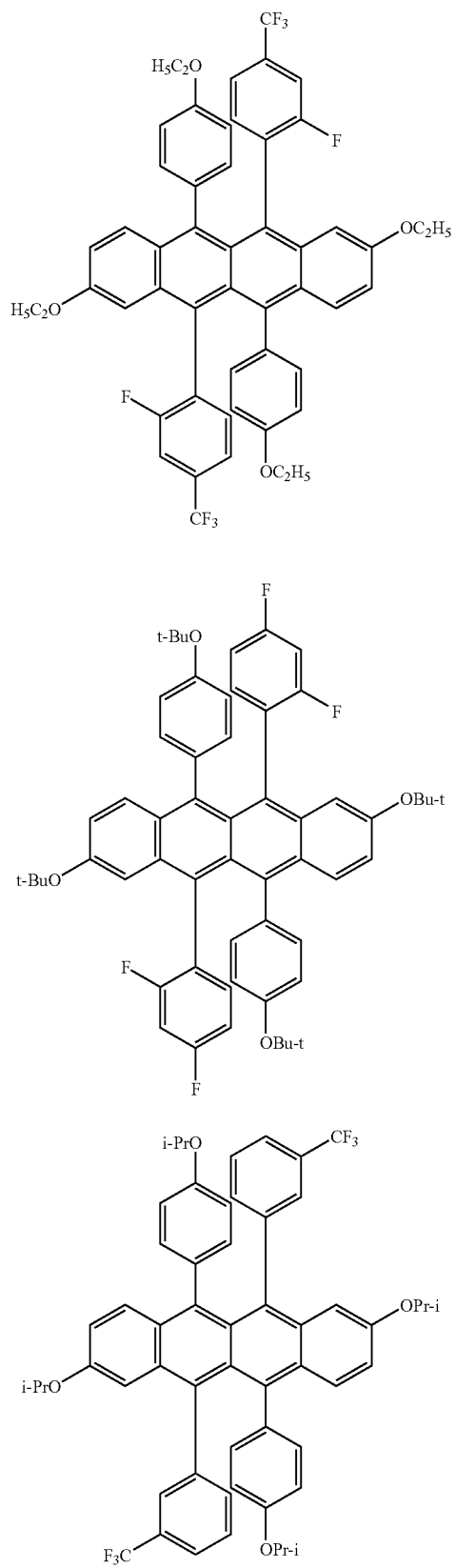
Inv-8
Inv-9
-continued
Inv-10
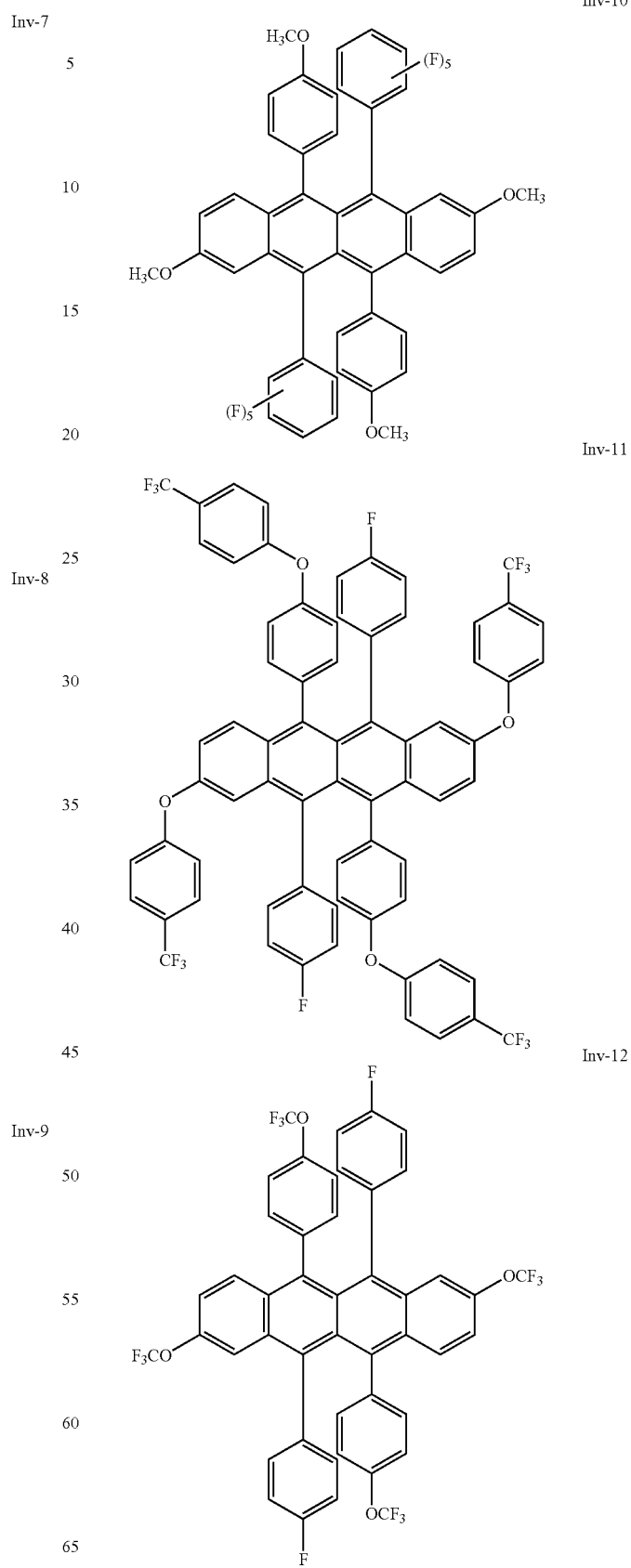
Inv-11
Inv-12

-continued

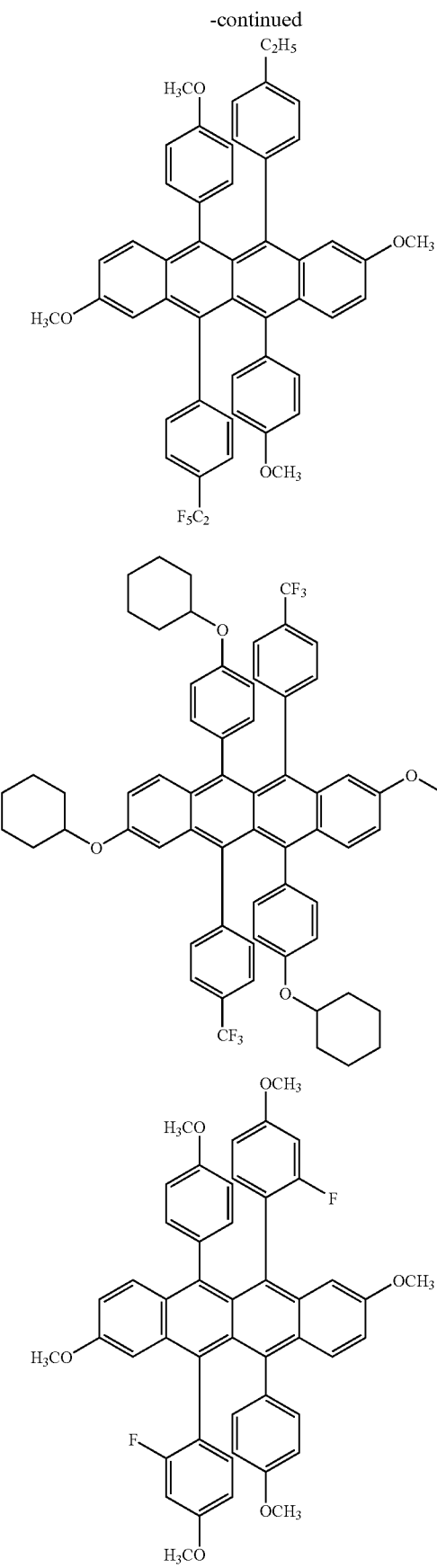

Inv-13

Inv-14

Inv-15

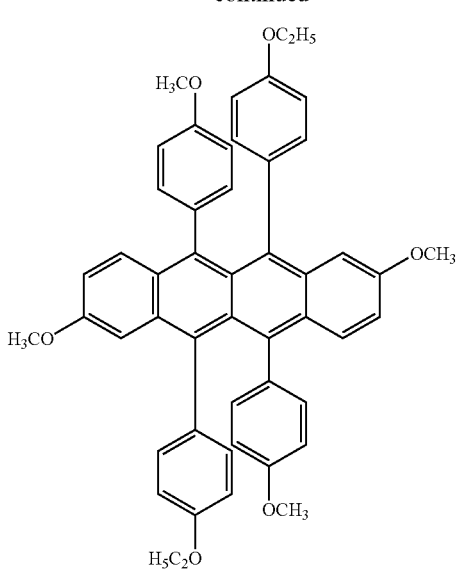

Inv-16

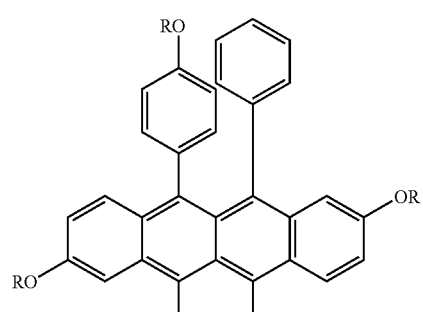

Inv-17

Embodiments of the invention provide not only emission $\lambda_{max}$ shifted to longer wavelength but also high luminance efficiency and a more desirable orange-red hue as evidenced by the location and shape of the absorption curve of the emitted light.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonyl amino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy) acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

General Device Architecture

The present invention can be employed in most OLED device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with a thin film transistor (TFT).

There are numerous configurations of the organic layers wherein the present invention can be successfully practiced. Essential requirements are a cathode, an anode, an HTL and an LEL. A more typical structure is shown in FIG. 1 and contains a substrate 101, an anode 103, an optional hole-injecting layer 105, a hole-transporting layer 107, a light-emitting layer 109, an electron-transporting layer 111, and a cathode 113. These layers are described in detail below. Note that the substrate may alternatively be located adjacent to the cathode, or the substrate may actually constitute the anode or cathode. Also, the total combined thickness of the organic layers is preferably less than 500 nm.

Substrate

The substrate 101 can either be light transmissive or opaque, depending on the intended direction of light emission. The light transmissive property is desirable for viewing the EL emission through the substrate. Transparent glass or organic materials are commonly employed in such cases. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, ceramics, and circuit board materials. Of course it is necessary to provide in these device configurations a light-transparent top electrode.

Anode

The conductive anode layer 103 is commonly formed over the substrate and, when EL emission is viewed through the anode, should be transparent or substantially transparent to the emission of interest. Common transparent anode materials used in this invention are indium-tin oxide (ITO) and tin oxide, but other metal oxides can work including, but not limited to, aluminum- or indium-doped zinc oxide (IZO), magnesium-indium oxide, and nickel-tungsten oxide. In addition to these oxides, metal nitrides, such as gallium nitride, and metal selenides, such as zinc selenide, and metal sulfides, such as zinc sulfide, can be used in layer 103. For applications where EL emission is viewed through the top electrode, the transmissive characteristics of layer 103 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes.

Hole-Injecting Layer (HIL)

While not always necessary, it is often useful that a hole-injecting layer 105 be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds such as those described in U.S. Pat. No. 4,720,432, and plasma-deposited fluorocarbon polymers such as those described in U.S. Pat. No. 6,208,075. Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a mono arylamine, diaryl amine, triarylamine, or a polymeric arylamine group. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural formula (A).

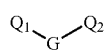

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring group, e.g., a naphthalene. When G is an aryl group, it is conveniently a phenylene, biphenylene, or naphthalene group.

A useful class of triarylamine groups satisfying structural formula (A) and containing two triarylamine groups is represented by structural formula (B):

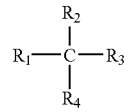

B where
  $R_1$ and $R_2$ each independently represents a hydrogen atom, an aryl group, or an alkyl group or $R_1$ and $R_2$ together represent the atoms completing a cycloalkyl group; and
  $R_3$ and $R_4$ each independently represents an aryl group, which is in turn substituted with a diaryl substituted amino group, as indicated by structural formula (C):

C wherein $R_5$ and $R_6$ are independently selected aryl groups. In one embodiment, at least one of $R_5$ or $R_6$ contains a polycyclic fused ring group, e.g., a naphthalene.

Another class of aromatic tertiary amine groups is the tetraaryldiamines. Desirable tetraaryldiamines groups include two diarylamino groups, such as indicated by formula (C), and linked through an arylene group. Useful tetraaryldiamines include those represented by formula (D).

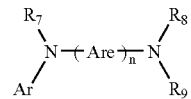

D wherein
  each Are is an independently selected arylene group, such as a phenylene or anthracene group,
  n is an integer of from 1 to 4, and
  Ar, $R_7$, $R_8$, and $R_9$ are independently selected aryl groups. In a typical embodiment, at least one of Ar, $R_7$, $R_8$, and $R_9$ is a polycyclic fused ring group, e.g., a naphthalene The various alkyl, alkylene, aryl, and arylene groups of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene groups typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene groups are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
4,4'-Bis(diphenylamino)quadriphenyl
Bis(4-dimethylamino-2-methylphenyl)-phenylmethane
N,N,N-Tri(p-tolyl)amine
4-(di-p-tolylamino)-4'-[4(di-p-tolylamino)-styryl]stilbene
N,N,N',N'-Tetra-p-tolyl-4-4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl
4,4'-Bis[N-(1-naphthyl)-N-(2-naphthyl)amino]biphenyl
4,4"-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4"-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis{N-phenyl-N-[4-(1-naphthyl)-phenyl]amino}biphenyl
4,4'-Bis[N-phenyl-N-(2-pyrenyl)amino]biphenyl
2,6-Bis[N,N-di(2-naphthyl)amine]fluorine
1,5-Bis[N-(1-naphthyl)-N-phenylamino]naphthalene Another class of useful hole-transporting materials includes polycyclic aromatic compounds as described in EP 1 009 041. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Light-Emitting Layer (LEL)

As more fully described in U.S. Pat. Nos. 4,769,292 and 5,935,721, the light-emitting layer (LEL) 109 of the organic EL element comprises a luminescent or fluorescent material where electroluminescence is produced as a result of electron-hole pair recombination in this region. The light-emitting layer can be comprised of a single material, but more commonly consists of a host material doped with a guest compound or compounds where light emission comes primarily from the dopant and can be of any color. The host materials in the light-emitting layer can be an electron-transporting material, as defined below, a hole-transporting material, as defined above, or another material or combination of materials that support hole-electron recombination. The dopant is usually chosen from highly fluorescent dyes, but phosphorescent compounds, e.g., transition metal complexes as described in WO 98/55561, WO 00/18851, WO 00/57676, and WO 00/70655 are also useful. Dopants are typically coated as 0.01 to 10% by weight into the host material.

An important relationship for choosing a dye as a dopant is a comparison of the bandgap potential which is defined as the energy difference between the highest occupied molecular orbital and the lowest unoccupied molecular orbital of the molecule. For efficient energy transfer from the host to the dopant molecule, a necessary condition is that the band gap of the dopant is smaller than that of the host material.

Host and emitting molecules known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

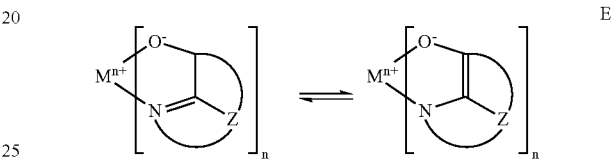

E wherein
M represents a metal;
n is an integer of from 1 to 4; and
Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc (II)
CO-4: Bis(2-methyl-8-quinolinolato)aluminum(III)-μ-oxo-bis(2-methyl-8-quinolinolato) aluminum(III)
CO-5: Indium trisoxine [alias, tris(8-quinolinolato)indium]
CO-6: Aluminum tris(5-methyloxine) [alias, tris(5-methyl-8-quinolinolato) aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]
CO-10: Bis(2-methyl-8-quinolinato)-4-phenylphenolatoaluminum (III)

Derivatives of 9,10-di-(2-naphthyl)anthracene (Formula F) constitute one class of useful hosts capable of supporting electroluminescence, and are particularly suitable for light emission of wavelengths longer than 400 nm, e.g., blue, green, yellow, orange or red.

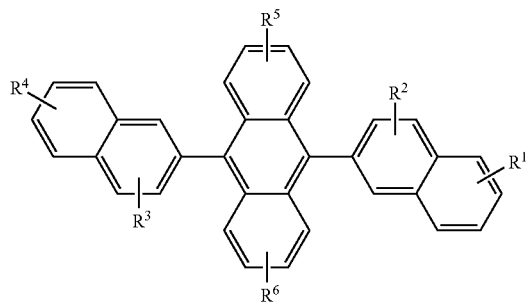

F wherein: $R^1$, $R^2$, $R^3$, $R^4$, $R^5$, and $R^6$ represent hydrogen or one or more substituents selected from the following groups:
Group 1: hydrogen, alkyl and alkoxy groups typically having from 1 to 24 carbon atoms;
Group 2: a ring group, typically having from 6 to 20 carbon atoms;
Group 3: the atoms necessary to complete a carbocyclic fused ring group such as naphthyl, anthracenyl, pyrenyl, and perylenyl groups, typically having from 6 to 30 carbon atoms;
Group 4: the atoms necessary to complete a heterocyclic fused ring group such as furyl, thienyl, pyridyl, and quinolinyl groups, typically having from 5 to 24 carbon atoms;
Group 5: an alkoxylamino, alkylamino, and arylamino group typically having from 1 to 24 carbon atoms; and
Group 6: fluorine, chlorine, bromine and cyano radicals.

Illustrative examples include 9,10-di-(2-naphthyl)anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene, and phenylanthracene derivatives as described in EP 681,019.

Benzazole derivatives (Formula G) constitute another class of useful hosts capable of supporting electroluminescence, and are particularly suitable for light emission of wavelengths longer than 400 nm, e.g., blue, green, yellow, orange or red.

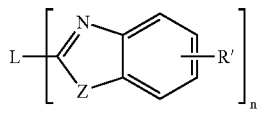

G where:
n is an integer of 3 to 8;
Z is —O, —NR or —S where R is H or a substituent; and
R' represents one or more optional substituents where R and each R' are H or alkyl groups such as propyl, t-butyl, and heptyl groups typically having from 1 to 24 carbon atoms; carbocyclic or heterocyclic ring groups such as phenyl and naphthyl, furyl, thienyl, pyridyl, and quinolinyl groups and atoms necessary to complete a fused aromatic ring group typically having from 5 to 20 carbon atoms; and halo such as chloro, and fluoro;

L is a linkage unit usually comprising an alkyl or ary group which conjugately or unconjugately connects the multiple benzazoles together.

An example of a useful benzazole is 2, 2', 2"-(1,3,5-phenylene)tris[1-phenyl-1H-benzimidazole].

Distyrylarylene derivatives as described in U.S. Pat. No. 5,121,029 are also useful host materials in the LEL.

Desirable fluorescent dopants include groups derived from fused ring, heterocyclic and other compounds such as anthracene, tetracene, xanthene, perylene, rubrene, coumarin, rhodamine, quinacridone, dicyanomethylenepyran, thiopyran, polymethine, pyrilium thiapyrilium, and carbostyryl compounds. Illustrative examples of useful dopants include, but are not limited to, the following:

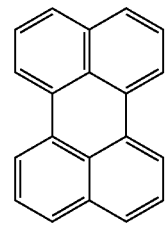

L1

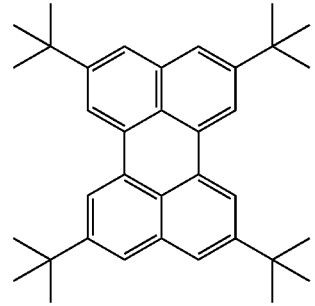

L2

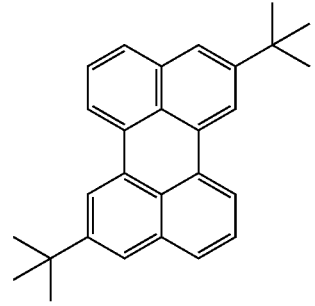

L3

-continued

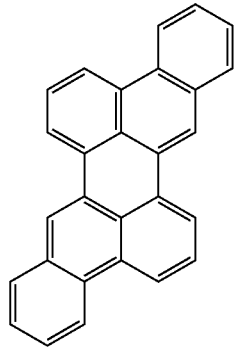

L4

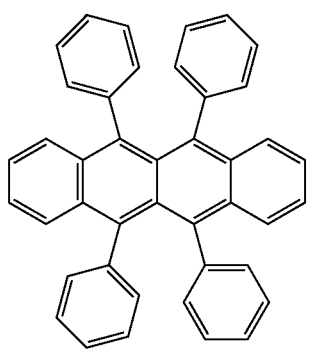

L5

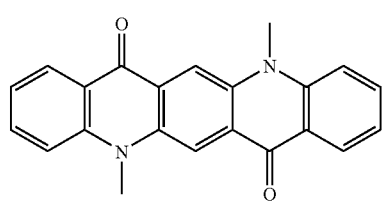

L6

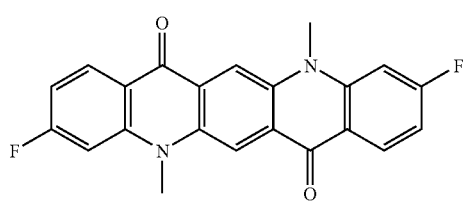

L7

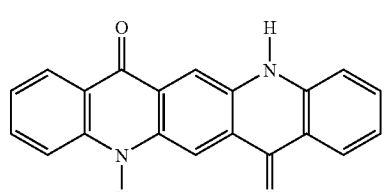

L8

-continued

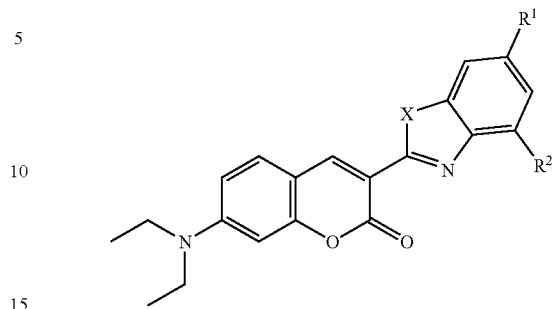

| | X | R1 | R2 |
| --- | --- | --- | --- |
| L9 | O | H | H |
| L10 | O | H | Methyl |
| L11 | O | Methyl | H |
| L12 | O | Methyl | Methyl |
| L13 | O | H | t-butyl |
| L14 | O | t-butyl | H |
| L15 | O | t-butyl | t-butyl |
| L16 | S | H | H |
| L17 | S | H | Methyl |
| L18 | S | Methyl | H |
| L19 | S | Methyl | Methyl |
| L20 | S | H | t-butyl |
| L21 | S | t-butyl | H |
| L22 | S | t-butyl | t-butyl |

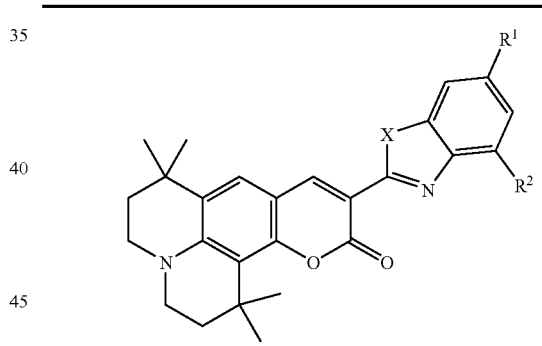

| | X | R1 | R2 |
| --- | --- | --- | --- |
| L23 | O | H | H |
| L24 | O | H | Methyl |
| L25 | O | Methyl | H |
| L26 | O | Methyl | Methyl |
| L27 | O | H | t-butyl |
| L28 | O | t-butyl | H |
| L29 | O | t-butyl | t-butyl |
| L30 | S | H | H |
| L31 | S | H | Methyl |
| L32 | S | Methyl | H |
| L33 | S | Methyl | Methyl |
| L34 | S | H | t-butyl |
| L35 | S | t-butyl | H |
| L36 | S | t-butyl | t-butyl |

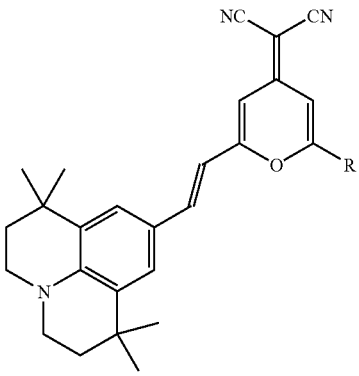

| | R |
|---|---|
| L37 | phenyl |
| L38 | methyl |
| L39 | t-butyl |
| L40 | mesityl |

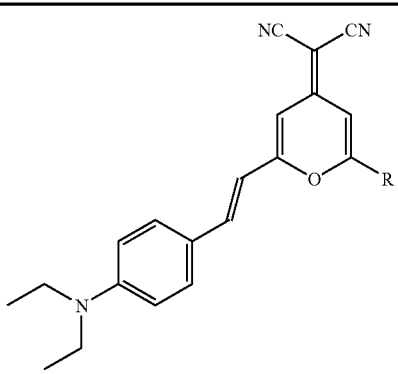

| | R |
|---|---|
| L41 | phenyl |
| L42 | methyl |
| L43 | t-butyl |
| L44 | mesityl |

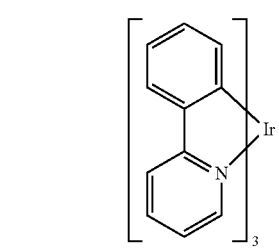

L45

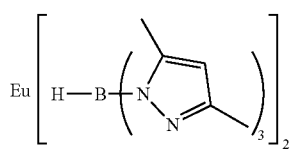

L46

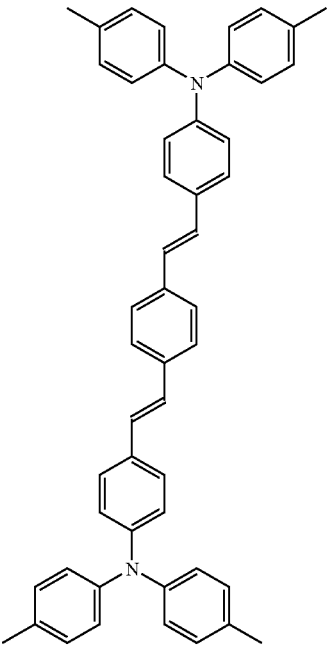

L47

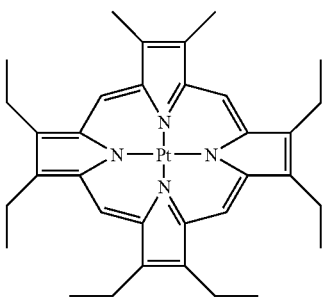

L48

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials.

In some instances, layers 109 and 111 can optionally be collapsed into a single layer that serves the function of supporting both light emission and electron transportation.

Cathode

When light emission is through the anode, the cathode layer 113 used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One preferred cathode material is comprised of a Mg:Ag alloy wherein the percentage of silver is in the range of 1 to 20%, as described in U.S. Pat. No. 4,885,221. Another suitable class of cathode materials includes bilayers comprised of a thin layer of a low work function metal or metal salt capped with a thicker layer of conductive metal. One such cathode is comprised of a thin layer of LiF followed by a thicker layer of Al as described in U.S. Pat. No. 5,677,572. Other useful cathode materials include, but are not limited to, those disclosed in U.S. Pat. Nos. 5,059,861, 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. No. 5,776,623. Cathode materials can be deposited by evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Deposition of Organic Layers

The organic materials mentioned above are suitably deposited through sublimation, but can be deposited from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,851,709 and 6,066,357) and inkjet method (U.S. Pat. No. 6,066,357).

Encapsulation

Most OLED devices are sensitive to moisture and/or oxygen so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890.

The entire contents of the patents and other publications referred to in this specification are incorporated herein by reference.

EXAMPLES

The inventions and its advantages are further illustrated by the specific examples, which follow.

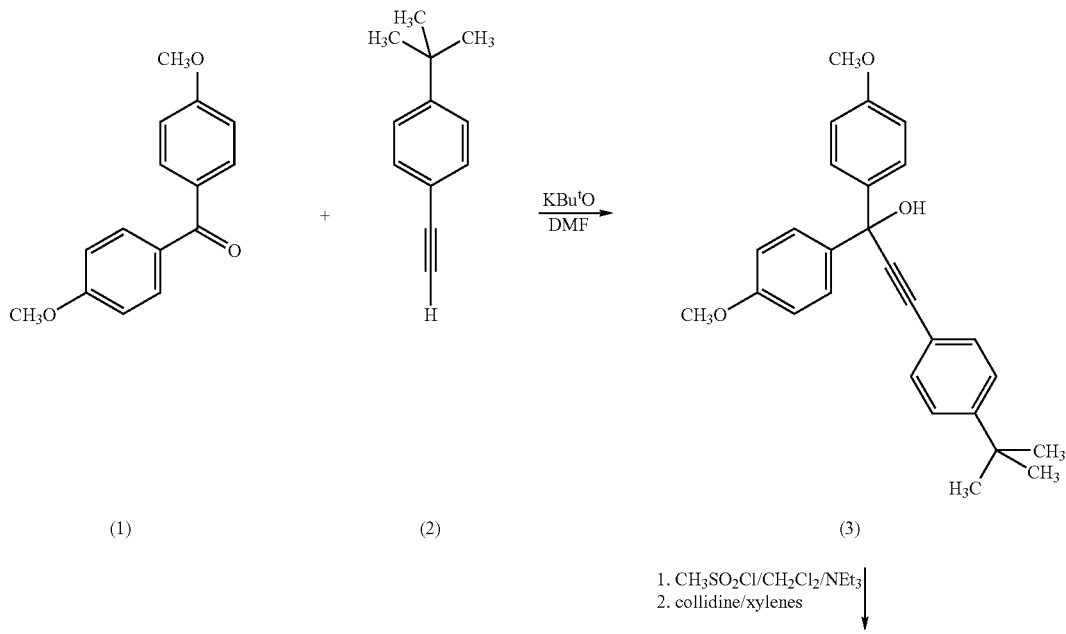

-continued

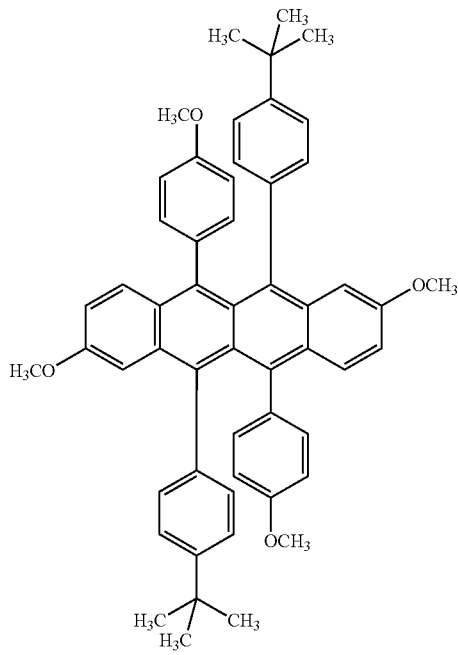

(Inv-3)

Example 1

Synthesis (Scheme 1)

Preparation of Compound (3): Under a nitrogen atmosphere, acetylenic compound (2) (6.32 g, 40 mMole), was dissolved in dimethylformamide (DMF) (200 mL) and the solution cool to 0° C. Potassium t-butoxide (KBu$^t$O) (4.5 g, 40 mMole), was added and the mixture stirred well for approximately 15 minutes. To this mixture was then added the benzophenone (1) (9.69 g, 40 mMole). Stirring was continued at 0° C. for approximately 30 minutes and then allowed to come to room temperature over a 1-hour period. At the end of this time the solution was cooled to 0° C. and the reaction treated with saturated sodium chloride (20 mL). The mixture was then diluted with ethyl acetate, washed with 2N-HCl (×3), dried over MgSO$_4$, filtered, concentrated under reduced pressure and the unreacted benzophenone (1) removed by filtration. The crude product was triturated with petroleum ether to give the product as an off-white solid. Yield of compound (3), 7.3 g.

Preparation of Inventive Compound, Inv-3: Compound (3) (6.7 g, 16.7 mMole) was dissolved in methylene chloride (CH$_2$Cl$_2$) (70 mL), and stirred at 0° C. under a nitrogen atmosphere. To this solution was added triethylamine (NEt$_3$) (1.69 g, 16.7 mMole) and then treated drop by drop with methanesulfonyl chloride (CH$_3$SO$_2$Cl) (2.14 g, 16.7 mMole), keeping the temperature of the reaction in the range 0–5° C. After the addition the solution was stirred at 0° C. for 30 minutes and then allowed to warm to room temperature over 1 hour. The reaction was then heated to reflux, distilling off the methylene chloride solvent and gradually replacing it with xylenes (a total of 70 mL). When the internal temperature of the reaction reached 80° C., collidine (2.02 g, 16.7 mMole), dissolved in xylenes (10 mL) was added drop by drop over a 10-minute period. The temperature was then raised to 110° C. and held at this temperature for 4 hours. After this period the reaction was cooled and the solid filtered off. This material was washed with xylenes and the washings concentrated under reduced pressure. The residue so obtained was stirred in methanol, filtered and the solid washed with a little ether. This gave Inv-3 as a bright red solid. Yield 1.4 g with a melting point of 265° C. The product may be further purified by sublimation (258° C. @ 200 millitorr) with a N$_2$ carrier gas.

Example 2

Wavelength of Maximum Emission

The wavelengths of maximum emission, or $\lambda_{max}$ of the compounds of the invention and comparative examples Comp-1 through Comp-4, were obtained by dissolving the compounds in ethyl acetate and recording the emission spectra in a fluorimeter. Table 1 shows that the comparison compounds have emission $\lambda_{max}$ values in the range 545–590 nm, whereas compounds of the invention show a desirable shift to longer wavelength and are in the range 592–594 nm. For purposes of comparison, the last column of Table 1 details the $\lambda_{max}$ of the material in a device obtained as described in Example 3 and Table 3.

The comparative compounds used in the invention are as follows:

Comp-1

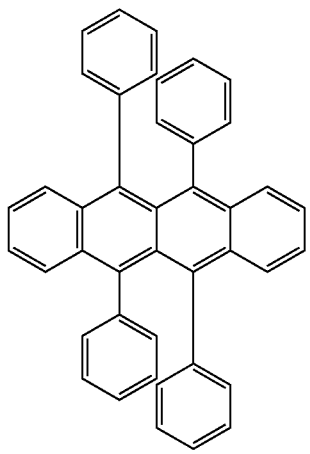

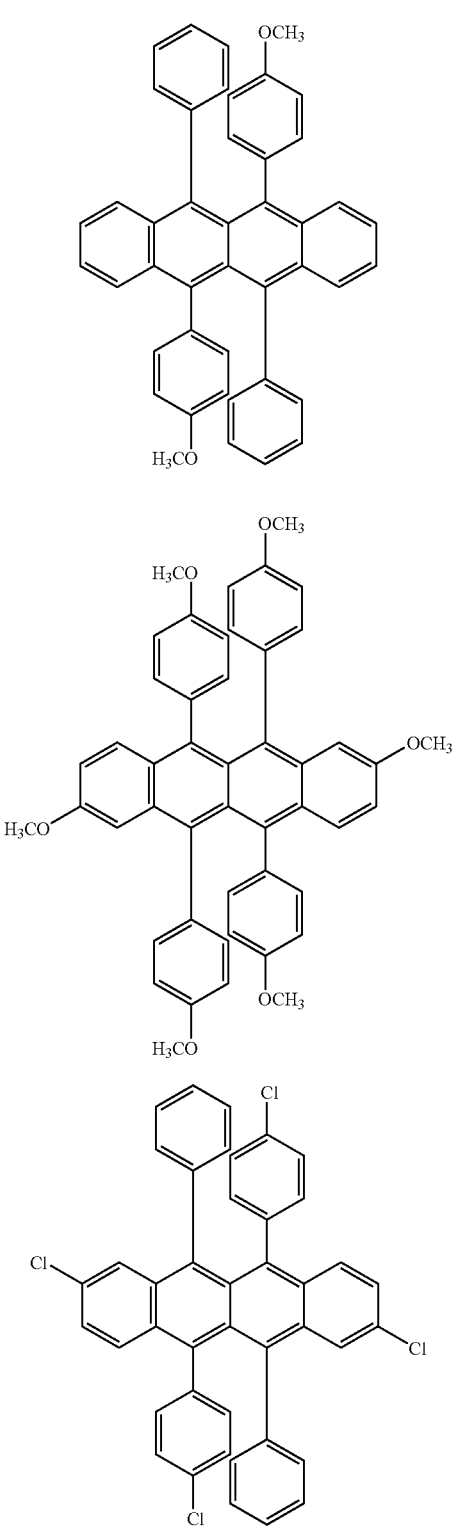

opposite to each other, but falls outside the scope of the current invention because it has no methoxy groups on the end rings of the naphthacene. Comp-2 is disclosed in JP04335087 as specific example 3 and Comp-3 is also disclosed in JP04335087 as specific example 4. Comp-4 was chosen to show that not all substituents on the end rings of the tetracene are capable of shifting the emission $\lambda_{max}$ to longer wavelength.

TABLE 1

Wavelength of Maximum Emission ($\lambda_{max}$).
(Ethyl acetate Solution)

| Sample | Type | Compound | $\lambda_{max}$ (nm) soln | $\lambda_{max}$ (nm) device |
|---|---|---|---|---|
| 1 | Inventive | Inv-1 | 592 | 592 |
| 2 | Inventive | Inv-2 | 594 | 592 |
| 3 | Inventive | Inv-3 | 592 | 592 |
| 4 | Inventive | Inv-4 | 592 | 592 |
| 5 | Inventive | Inv-5 | 592 | 576 |
| 6 | Comparative | Comp-1 | 556 | 568 |
| 7 | Comparative | Comp-2 | 545 | 568 |
| 8 | Comparative | Comp-3 | 590 | 568 |
| 9 | Comparative | Comp-4 | 558 | 564 |

As seen from Table 1, the comparatives provide $\lambda_{max}$ values in solution that are at or below the desired lower end of the range and in the device the values are lower than the minimum acceptable value of 570 nm.

Example 3

EL Device Fabrication

Inventive Example

An EL device satisfying the requirements of the invention was constructed as Sample 10 in the following manner:

A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.

a) Over the ITO was deposited a 1 nm fluorocarbon (CFx) hole-injecting layer (HIL) by plasma-assisted deposition of $CHF_3$.

b) A hole-transporting layer (HTL) of N,N'-di-1-naphthalenyl-N,N'-diphenyl-4, 4'-diaminobiphenyl (NPB) having a thickness of 150 nm was then evaporated from a tantalum boat.

c) A 37.5 nm light-emitting layer (LEL) of tris(8-quinolinolato)aluminum (III) ($AlQ_3$) and Inv-1 (1 and 2%-wt, see Tables 2 and 3) were then deposited onto the hole-transporting layer. These materials were also evaporated from tantalum boats.

d) A 37.5 nm electron-transporting layer (ETL) of tris(8-quinolinolato)aluminum (III) ($AlQ_3$) was then deposited onto the light-emitting layer. This material was also evaporated from a tantalum boat.

e) On top of the $AlQ_3$ layer was deposited a 220 nm cathode formed of a 10:1 volume ratio of Mg and Ag.

The above sequence completed the deposition of the EL device. The device was then hermetically packaged in a dry glove box for protection against ambient environment.

Samples 11 through 14 were EL devices incorporating Inv-2 through Inv-5 fabricated in an identical manner and at the same level, 1%-wt, as the example incorporating Inv-1.

Comp-1 is the parent rubrene. It is well known to those in the art and has no substituents at the 2- and 8-positions on either of the end rings of the naphthacene nucleus, nor on the four phenyl rings located on the center rings of the naphthacene. Comp-2 has methoxy substituents located on two of the four central phenyl rings of the naphthacene, diagonally Samples 15 through 17 are the comparative EL devices that were prepared from comparative compounds Comp-2 through Comp-4 maintaining the same device architecture and level as in the inventive examples. Samples 18 through 22 were El devices incorporating Inv-1 through Inv-5 and samples 23 through 26 were El devices incorporating Comp-1 through Comp-4, respectively, fabricated in an identical manner as the example incorporating Inv-1 but at 2%-wt. The cells thus formed were tested for emission $\lambda_{max}$ and efficiency (in the form of luminance yield), and the results are listed in Tables 2 and 3.

TABLE 2

Evaluation Results for EL devices.

| Sample | Type | Host | Dopant (1%) | $\lambda_{max}$ (nm) | Efficiency (cd/A)[1] |
|---|---|---|---|---|---|
| 10 | Inventive | ALQ$_3$ | Inv-1 | 584 | 8.48 |
| 11 | Inventive | " | Inv-2 | 584 | 8.64 |
| 12 | Inventive | " | Inv-3 | 584 | 7.54 |
| 13 | Inventive | " | Inv-4 | 584 | 6.92 |
| 14 | Inventive | " | Inv-5 | 572 | 6.95 |
| 15 | Comparative | " | Comp-2 | 568 | 6.32 |
| 16 | Comparative | " | Comp-3 | 564 | 8.37 |
| 17 | Comparative | " | Comp-4 | 564 | 5.54 |

[1]Luminance yields reported at 20 mA/cm$^2$.

TABLE 3

Evaluation Results for EL devices.

| Sample | Type | Host | Dopant (2%) | $\lambda_{max}$ (nm) | Efficiency (cd/A)[1] |
|---|---|---|---|---|---|
| 18 | Inventive | ALQ$_3$ | Inv-1 | 592 | 5.73 |
| 19 | Inventive | " | Inv-2 | 592 | 5.0 |
| 20 | Inventive | " | Inv-3 | 592 | 6.02 |
| 21 | Inventive | " | Inv-4 | 592 | 5.01 |
| 22 | Inventive | " | Inv-5 | 576 | 7.53 |
| 23 | Comparative | " | Comp-1 | 568 | 5.94 |
| 24 | Comparative | " | Comp-2 | 568 | 6.74 |
| 25 | Comparative | " | Comp-3 | 568 | 6.73 |
| 26 | Comparative | " | Comp-4 | 564 | 5.54 |

[1]Luminance yields reported at 20 mA/cm$^2$.

As can be seen from Table 2, all tested EL devices incorporating the dopants of the invention at 1%-wt of the host, demonstrated high luminance yields. These doped EL devices exhibit orange-red electroluminescence with $\lambda_{max}$ ranging from 572–584 nm. In contrast, the EL devices incorporating the comparative dopants exhibited electroluminescence with $\lambda_{max}$ ranging from 564–568 nm. Table 3 shows all tested EL devices incorporating the dopants of the invention at 2%-wt of the host. At this level dopants of the invention also show good luminance yields and the $\lambda_{max}$ of the electroluminescence is in the range 576–592 nm. In contrast, the EL devices incorporating the comparative dopants at 2%-wt exhibited electroluminescence with $\lambda_{max}$ only in the range of 564–568 nm. The dopants of the invention are superior to the comparative dopants because they emit light shifted to longer wavelength.

PARTS LIST

| 101 | Substrate |
| 103 | Anode |
| 105 | Hole-Injecting layer (HIL) |
| 107 | Hole-Transporting layer (HTL) |
| 109 | Light-Emitting layer (LEL) |
| 111 | Electron-Transporting layer (ETL) |
| 113 | Cathode |

What is claimed is:

1. An OLED device comprising a light-emitting layer (LEL) containing a host and an emitting dopant located between a cathode and an anode wherein the dopant is an orange-red light emitting rubrene derivative represented by formula (I):

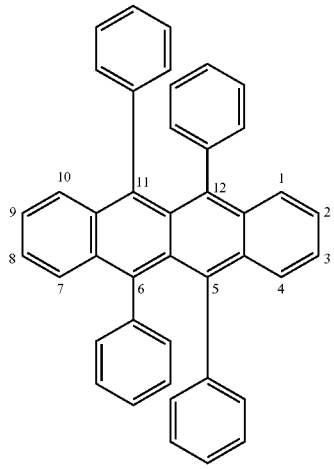

Formula (I)

wherein:
a) there are identical oxy, aza or thio groups at the 2- and 8-positions;
b) the phenyl rings in the 5- and 11-positions contain only para-substituents identical to the oxy, aza or thio groups in paragraph a);
c) the phenyl rings in the 6- and 12-positions are substituted or unsubstituted; and provided that when a single substituent is present on both phenyl rings in paragraph c), said substituent is not a methoxy group located at the para-position, and provided that all of the substituents are selected so that the wavelength of maximum emission ($\lambda_{max}$) in the EL device is such that 570 nm$<\lambda_{max}\leq$650 nm.

2. The device of claim 1 comprising a further light-emitting compound to provide a white light emission.

3. The device of claim 2 further comprising a blue light-emitting compound to provide a white light emission.

4. The device of claim 2 further comprising a filter over-lying the device.

5. The device of claim 2 wherein the layer comprises a host and dopant where the dopant is present in an amount of up to 10%-wt of the host.

6. The device of claim 5 wherein the dopant is present in an amount of 0.1–5.0%-wt of the host.

7. The device of claim 1 wherein the dopant is represented by formula (IV):

Formula (IV)

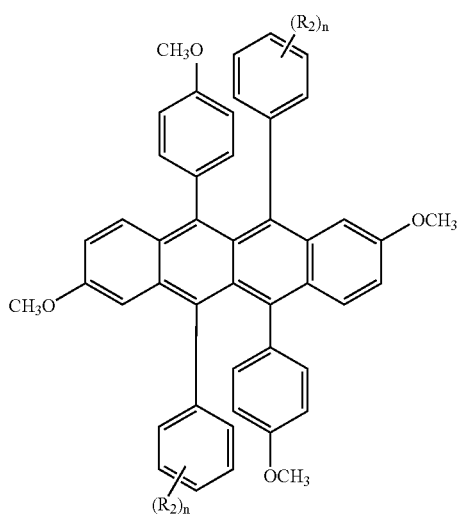

wherein
R$_2$ is a substituent group;
n is 0–5;
provided that the R$_2$, their location and n value on one ring are the same as those on the second ring; and
provided further that when n is 1, R$_2$ is not para-methoxy.

8. The device of claim 1 wherein the host is an amine compound.

9. The device of claim 1 wherein the host comprises N,N'-di-1-naphthalenyl-N,N'-diphenyl-4,4'-diaminobiphenyl.

10. The device of claim 1 wherein the substituents are selected to provide a reduced loss of initial luminance compared to the device containing no rubrene compound.

11. The device of claim 1 wherein the rubrene compound is selected from the following:

Inv-1

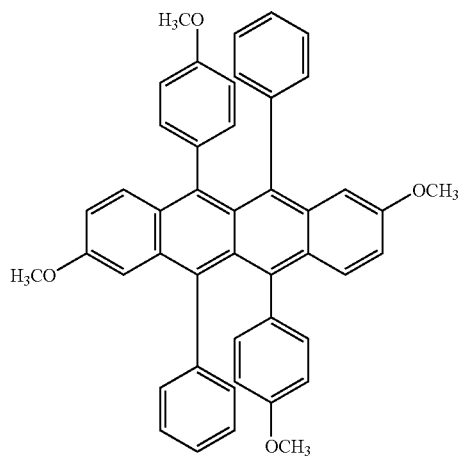

-continued

Inv-2

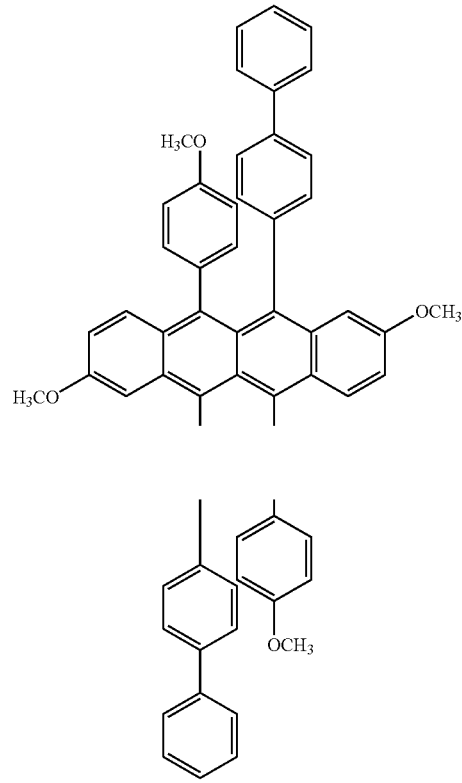

Inv-3

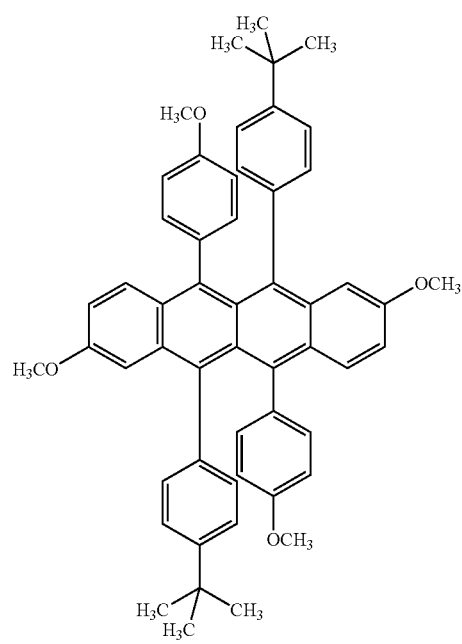

-continued
Inv-4
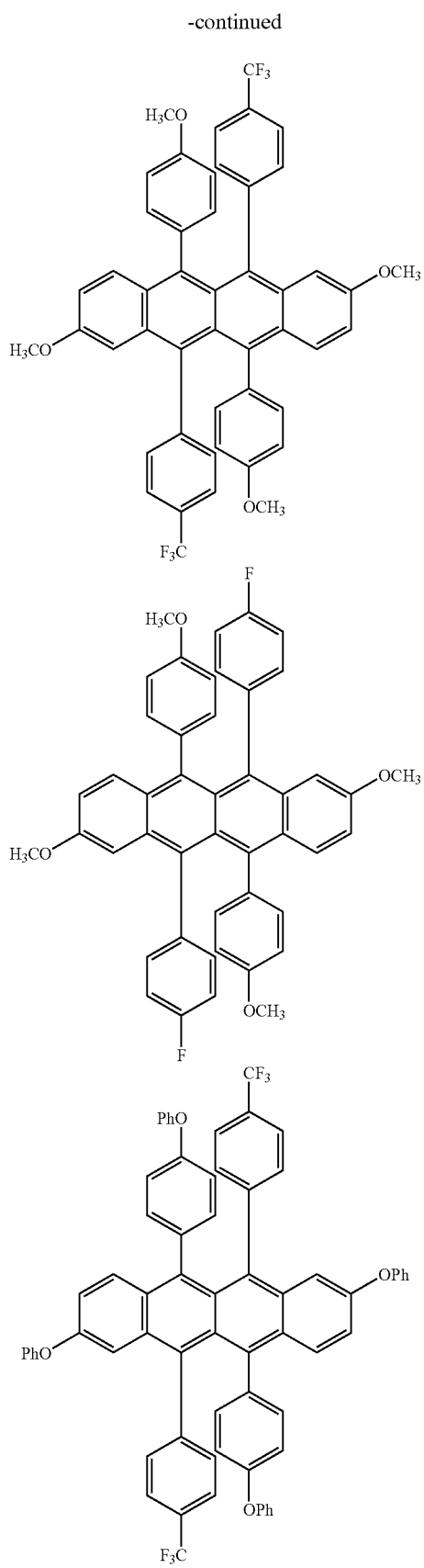
Inv-5
Inv-6
-continued
Inv-7
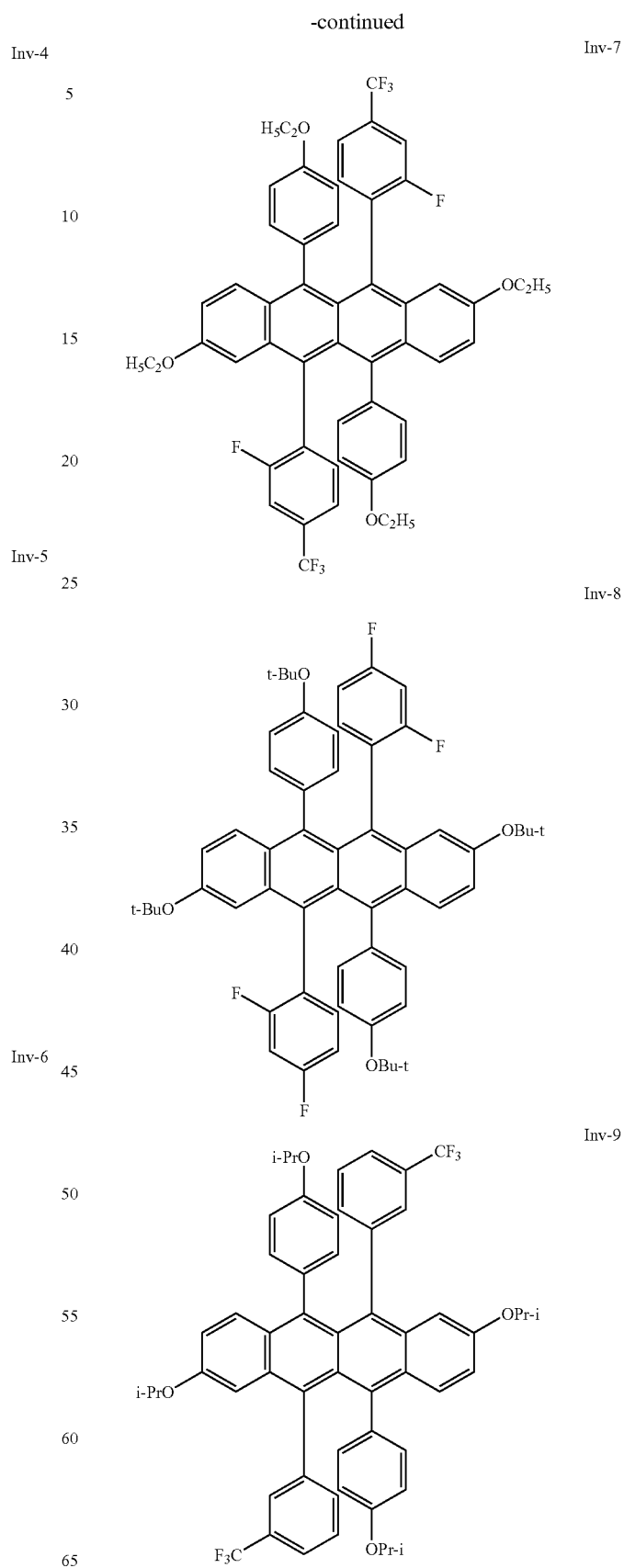
Inv-8
Inv-9

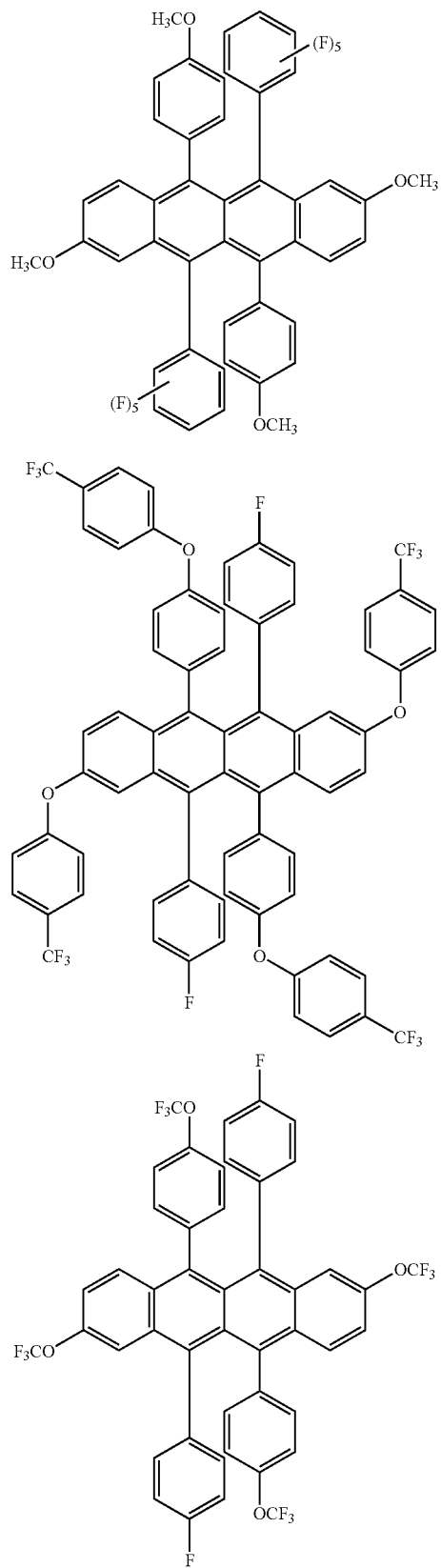
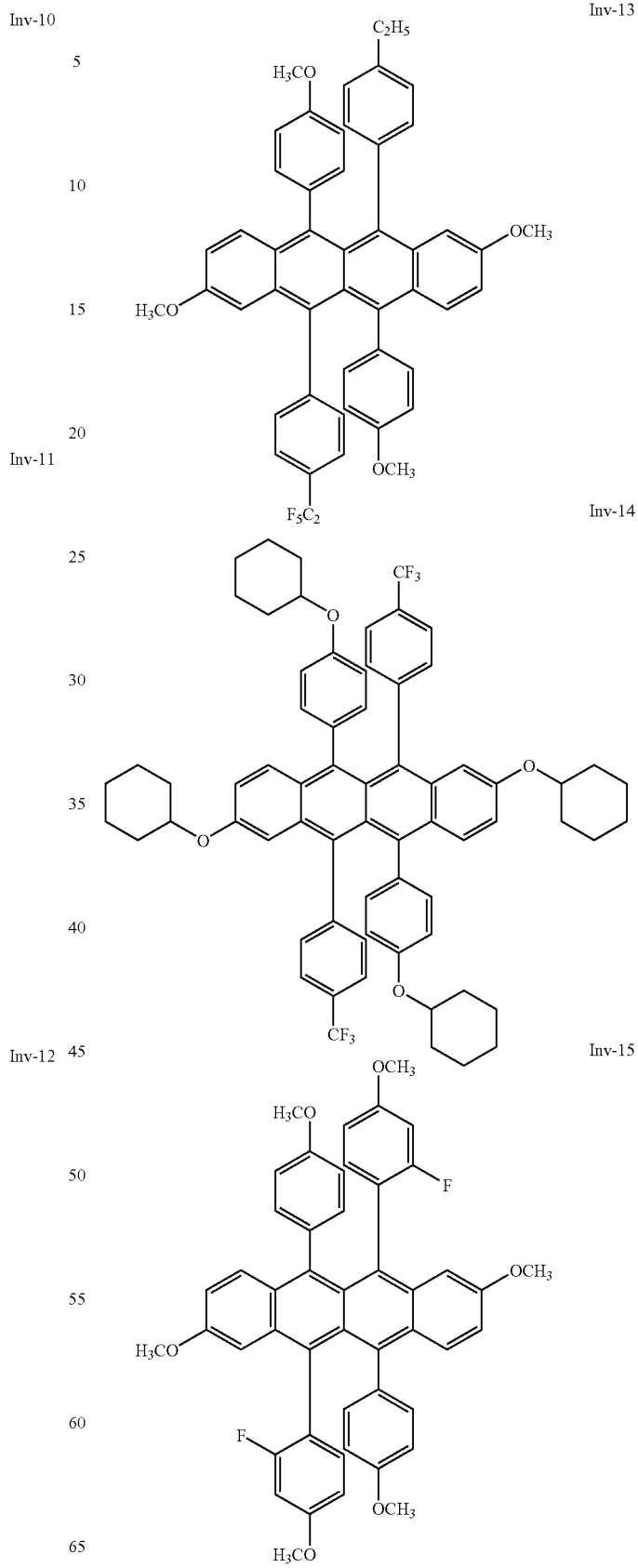

-continued

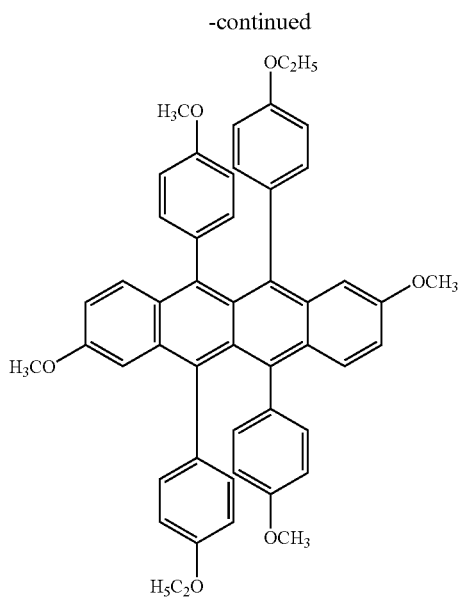
Inv-16

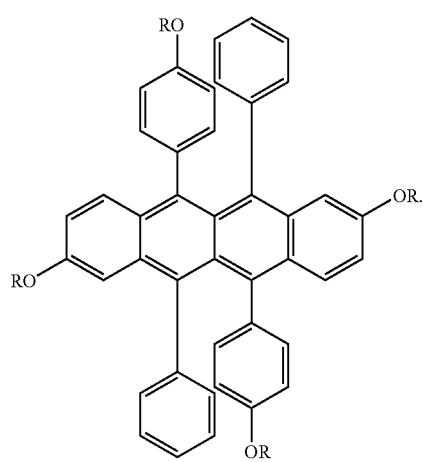
Inv-17

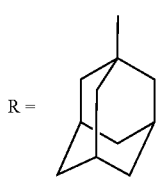

12. A light emitting device containing the OLED device of claim 1.

13. A light-emitting display containing the OLED device of claim 1.

14. A method of emitting light comprising subjecting the device of claim 1 to an applied voltage.

15. An OLED device comprising a light-emitting layer (LEL) containing a host and an emitting dopant located between a cathode and an anode wherein the dopant is an orange-red light emitting rubrene derivative represented by formula (II):

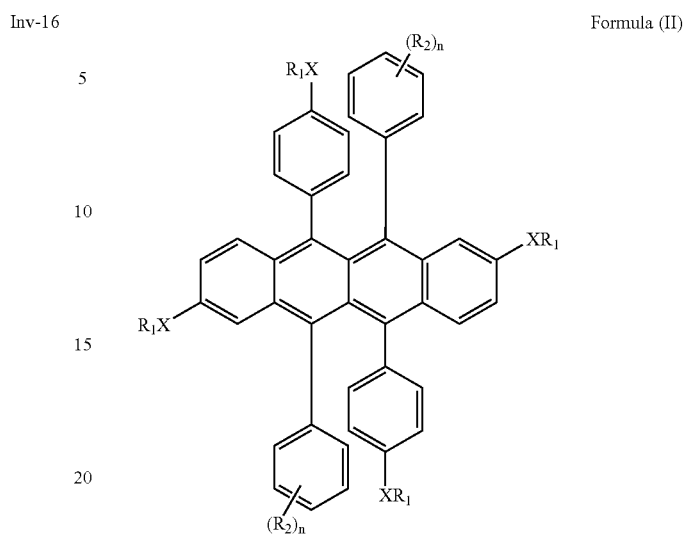
Formula (II)

wherein
R₁ is selected from alkyl, carbocyclic, and heterocyclic groups;
R₂ is a substituent group;
X is oxygen, sulfur or N(R₃) wherein R₃ is selected from alkyl, carbocyclic and heterocyclic groups or taken with R₁ may form a ring;
n is 0–5;
provided that all R₁ groups are the same;
provided further, that the R₂ substituents, their location and n value on one ring, are the same as those on the second ring; and
provided still further that when X is oxygen and n is 1, R₂ is not para-methoxy, and provided that all of the substituents are selected so that the wavelength of maximum emission ($\lambda_{max}$) in the EL device is such that 570 nm<$\lambda_{max}$≦650 nm.

16. The device of claim 15 wherein the dopant is represented by formula (III):

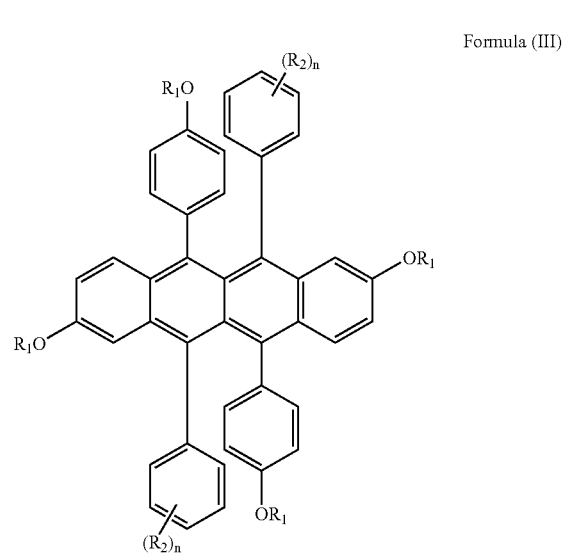
Formula (III)

wherein
R₁ is selected from alkyl, carbocyclic, and heterocyclic groups;
R₂ is a substituent group;
n is 0–5;
provided that all R₁ groups are the same;
provided further, that the R₂, their location and n value on one ring are the same as those on the second ring; and
provided still further that when n is 1, R₂ is not para-methoxy.

17. The device of claim 15 wherein R₁ is a carbocyclic or heterocyclic group.

18. The device of claim 15 wherein R₁ is an alkyl or aryl group.

19. The device of claim 15 wherein R₁ is represented by the formula;

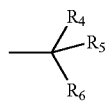

wherein each of R₄, R₅ and R₆ is hydrogen or an independently selected substituent.

20. The device of claim 19 wherein R₄, R₅ and R₆ taken together may form a mono- or multi-cyclic ring system.

21. The device of claim 15 wherein R₁ is represented by the formula;

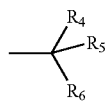

wherein each of R₄, R₅ and R₆ is hydrogen or an independently selected substituent with no more than one being hydrogen.

22. The device of claim 15 comprising a further light-emitting compound to provide a white light emission.

23. The device of claim 22 further comprising a blue light-emitting compound to provide a white light emission.

24. The device of claim 22 further comprising a filter over-lying the device.

25. The device of claim 15 wherein R₂ is located in meta and para positions of the phenyl group.

26. The device of claim 15 wherein R₂ is phenyl.

27. The device of claim 15 wherein R₂ is tert-butyl.

28. The device of claim 15 wherein R₂ is selected from fluorine, trifluoromethyl, pentafluoroethyl and fluorinated-phenyl groups.

29. The device of claim 15 wherein R₂ is a fluorine-containing group.

30. The device of claim 15 wherein R₂ is fluorine.

31. The device of claim 15 wherein R₁ is a fluorine-containing group.

32. The device of claim 15 wherein R₂ are independently selected from the group consisting of fluorine, fluorine containing groups, alkyl, aryl, alkoxy and aryloxy groups.

33. The device of claim 15 wherein the layer comprises a host and dopant where the dopant is present in an amount of up to 10%-wt of the host.

34. The device of claim 33 wherein the dopant is present in an amount of 0.1–5.0%-wt of the host.

35. An OLED device comprising a light-emitting layer (LEL) containing a host and an emitting dopant located between a cathode and an anode wherein the dopant is an orange-red light emitting rubrene derivative represented by formula (I):

Formula (I)

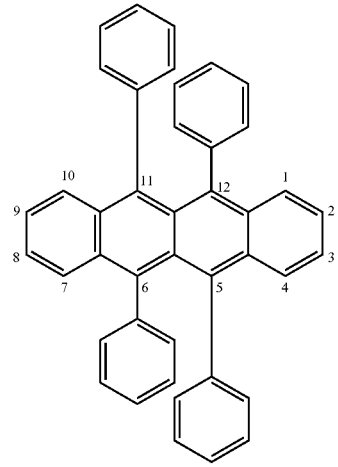

wherein:
a) there are identical oxy, aza or thio groups at the 2- and 8-positions;
b) the phenyl rings in the 5- and 11-positions contain only para-substituents identical to the oxy, aza or thio groups in paragraph a);
c) the phenyl rings in the 6- and 12-positions are substituted or not; and
provided that the rubrene derivative has a wavelength of maximum emission ($\lambda_{max}$) in ethyl acetate solution such that 560 nm$<\lambda_{max}\leq$650 nm and a wavelength of maximum emission ($\lambda_{max}$) in the EL device such that 570 nm$<\leq$650 nm.

36. An OLED device of claim 35 wherein the rubrene derivative has a wavelength of maximum emission ($\lambda_{max}$) in ethyl acetate solution such that 565 nm$<\lambda_{max}\leq$625 nm and a wavelength of maximum emission ($\lambda_{max}$) in the EL device such that 570 nm$<\lambda_{max}\leq$650 nm.

* * * * *